US00PP35502P2

(12) United States Plant Patent
Korlipara

(10) Patent No.: US PP35,502 P2
(45) Date of Patent: Nov. 21, 2023

(54) ***PENSTEMON* PLANT NAMED 'FLOCK OF FLAMINGOS'**

(50) Latin Name: ***Penstemon* spp.**
Varietal Denomination: Flock of Flamingos

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/116,026

(22) Filed: Mar. 1, 2023

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
CPC ..... A01H 5/02
See application file for complete search history.

(56) References Cited

PUBLICATIONS https://www.floraldaily.com/article/9397279/terra-nova-nurseries-introduces-sneak-peek-of-penstemon-flock-of-flamingos/; Feb. 4, 2022; 3 pages.*
https://www.greenhousegrower.com/crops/28-sun-loving-varieties-to-consider-for-2023/#slide=160732-160753-5; Aug. 30, 2022; 1 page.*
https://www.greenhousemag.com/article/2022-trial-standouts/; Nov. 2022; 2 pages.*
https://www.youtube.com/watch?v=O2Hwm9W8j40; Feb. 12, 2023; 2 pages.*
https://issuu.com/ehrpublications/docs/ehr_hot_new_perennials_2023_7-23-22_; Jul. 23, 2022; 1 page.*
https://www.bfgsupply.com/media/6179/2022-2023-terra-nova-product-program.pdf; 2022-2023; 11 pages.*
https://irp.cdn-website.com/42122c9a/files/uploaded/Michells-2023Catalog-sm.pdf; 2023; 122 pages.*
https://static1.squarespace.com/static/548b6971e4b0af3bfe38cd6f/t/63f9456df0201d3694999602/1677280622097/New+plants+for+2023.docx.pdf; 2023; 14 pages.*
https://www.canr.msu.edu/hrt/our_gardens/Visit/Amien-and-Florence-Carter-Trial-Garden/2022%20Trial%20Booklet; 2022; 41 pages.*
https://www.zyromski.com/media/wysiwyg/SFZ_BDC_-_2022-2023_DANZIGER_KD_1.pdf; Jun. 27, 2023; 20 pages.*
https://wholesale.devangh.ca/wp-content/uploads/2022/08/Young-Plants-Program-2022-2023-WEBSITE.pdf; Jun. 27, 2023; 67 pages.*

* cited by examiner

*Primary Examiner* — Kent L Bell
(74) *Attorney, Agent, or Firm* — The Webb Law Firm

(57) ABSTRACT

A new and distinct *Penstemon* plant characterized by its large, rose-pink flowers with a clean white throat, dense flower clusters, long bloom time, a strong, upright, and well branched habit with approximately 12 crowns from the base, clean-looking, deep green, and attractive foliage, and excellent vigor.

2 Drawing Sheets

Botanical classification: *Penstemon* spp.
Varietal denomination: 'Flock of Flamingos'.

BACKGROUND OF THE NEW PLANT

The present invention comprises a new and distinct *Penstemon* plant, of the family Scrophulariaceae, having the varietal name 'Flock of Flamingos'. The new variety originated as an open-pollinated cross in July of 2017 in the breeding fields of the applicant in Canby, Oregon using *Penstemon* plant named 'Strawberry Taffy' (U.S. Plant Pat. No. PP22,569) as the seed parent. 'Strawberry Taffy' is a complex hybrid, utilizing the *hartwegii* species. 'Flock of Flamingos' was selected for its medium-large, upright growth habit, large flowers in dense clusters, long flowering time, high vigor, and attractive foliage.

When compared to its seed parent, *Penstemon* plant named 'Strawberry Taffy', the new variety has a longer bloom time, larger and longer inflorescences, more stems from the crown, and a more upright growth habit. When compared to *Penstemon* plant named 'Cha Cha Pink' (U.S. Plant Pat. No. PP26,673), the new variety has a much larger habit, larger flowers with a brighter pink color and an unstriped throat, and numerous basal branches.

The new variety has only been reproduced by asexual propagation (cuttings and micropropagation using standard micropropagation practices). Each of the progeny exhibits identical characteristics to the original plant. Asexual propagation by cuttings and micropropagation using terminal and lateral shoots was first performed in late June of 2019 in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Penstemon* plants known to the breeder, the new variety is characterized by the following:

1. Large rose-pink flowers with clean white throats;
2. Large, dense flower clusters;
3. Long bloom time;
4. Large, upright, and well-branched habit, with approximately 12 crowns from the base;

5. Attractive foliage; and
6. High vigor.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
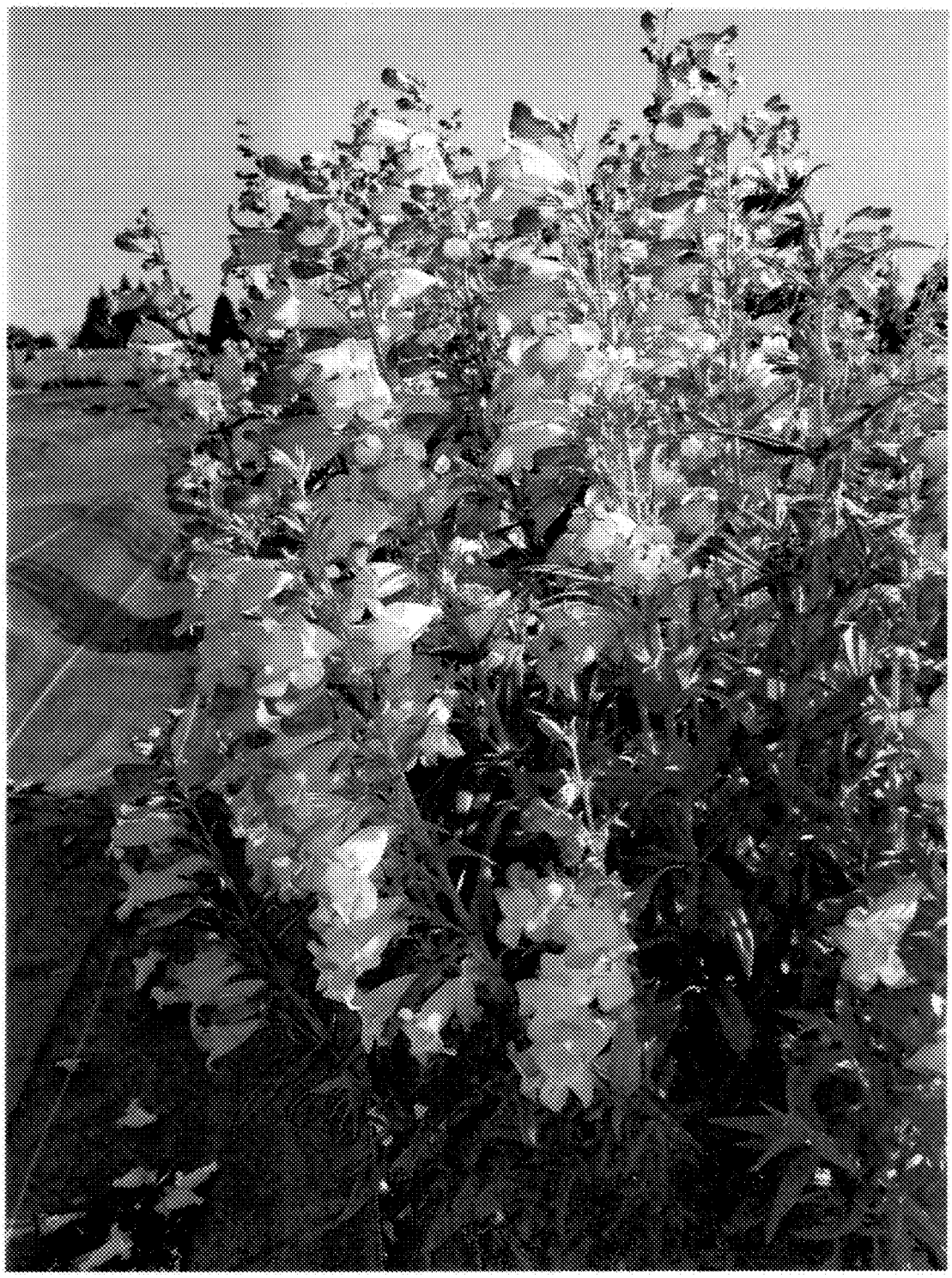
FIG. 1 illustrates an 18-month-old plant of the new variety in Canby, Oregon in late spring.
Figure 2:
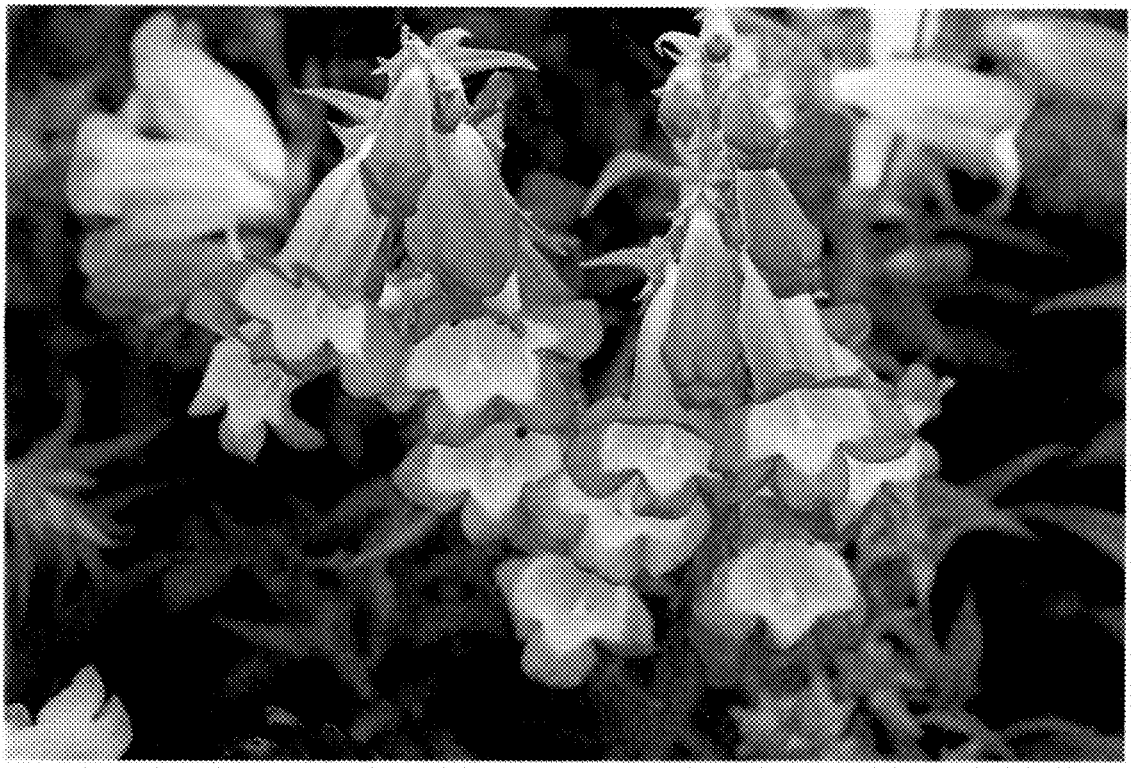
FIG. 2 illustrates a close-up of view of the flowers of a 2-year-old plant of the new variety in Canby, Oregon in September.

The following is a detailed description of the new variety based on observations of 2-year-old plants grown outside in trial beds in Canby, Oregon (USDA Zone 8). Temperatures range from a high of 35° C. in August to a low of 0° C. in January. Normal rainfall in Canby, Oregon is around 1 m per year. Color references are based on The 2007 R.H.S. Colour Chart of The Royal Horticultural Society of London, $5^{th}$ Edition.

Plant:

*Type.*—Herbaceous perennial.
*Hardiness.*—USDA Zones 7 to 10.
*Size.*—50.0 cm wide and 85.0 cm tall.
*Form.*—Upright, branching.
*Vigor.*—Very high.
*Root description.*—Fibrous and free branching. RHS 157D near crown to RHS NN155B at root hairs.
*Stem.*—Number: 12 stems from the crown. Form: Upright. Length: To 48.0 cm. Width: 5.0 mm at the base. Texture: Pubescent. Internode length: To 5.0 cm. Color: RHS 147B.

Foliage:

*Type.*—Simple.
*Leaf arrangement.*—Opposite.
*Shape.*—Lanceolate.
*Length.*—To 14.0 cm.
*Width.*—To 6.0 cm.
*Margin.*—Entire to sparsely denticulate.
*Apex.*—Acuminate.
*Base.*—Sessile.
*Leaf texture (both surfaces).*—Glabrous.
*Upper surface color.*—RHS 137A.
*Lower surface color.*—RHS 137D.
*Venation.*—Pinnate.

Flowers:

*Bud.*—Length: 3.5 cm. Width: 15.0 mm. Shape: Closed tubular, bulging, and flattened ventrally. Color: Primarily RHS NN155A, except for the presence of RHS 61C on lobes and at the base.
*Type.*—Zygomorphic, perfect.
*Shape.*—Tubular, bilabiate.
*Flower size.*—To 4.5 cm long and 4.0 cm wide.
*Inflorescence type.*—Terminal, many flowered, dense thyrse.
*Flower number per inflorescence.*—Average of 32.
*Inflorescence size.*—To 28.0 cm long and 10.0 cm wide.
*Bloom period.*—May through October in Canby, Oregon.
*Lastingness.*—Individual flowers last 5 to 6 days on the plant. Entire inflorescence lasts approximately 6 to 7 weeks, depending upon weather.
*Fragrance.*—None.
*Peduncle.*—Length: 3.0 cm. Width: 1.5 mm. Texture: Pubescent. Color: RHS N144A with a tint of RHS 58A in the sun.
*Pedicel.*—Length: 1.0 cm. Width: 1.0 mm. Texture: Pubescent. Color: RHS N144C with a tint of RHS 58A in the sun.
*Corolla.*—Length: 4.5 cm. Width: 4.2 cm. Description: Tube is funnelform in the calyx and measures 6.0 mm long and 4.0 mm wide, inflating to 30.0 mm long to 27.0 mm wide and flaring into 5 lobes. The two smaller, top lobes flare back (measuring 18.0 mm wide and 18.0 mm deep), the two larger, lateral lobes flare out (measuring 22.0 mm wide and 20.0 mm deep), and the lower lobe flares down (measuring 18.0 mm wide and 18.0 mm deep). Lobes: Margins: Entire. Tips: Obtuse. Texture: Outside is pubescent; inside is glabrous. Color (outer suface): RHS N66B on top of funnel and top 2 lobe backs, RHS 63B on bottom 3 lobe backs, and RHS NN155C on funnel bottom. Color (inner surface): RHS N66B on ¾ of the tip end of lobes, 3 bottom lobes have a ring of RHS 60A which extends down their main vein, and the tube RHS NN155D.
*Calyx (sepals).*—Arrangement: 5 overlapping lobes cut to the base, each lobe broadly ovate in shape and 10.0 mm deep and 9.0 mm wide. Size: 10.0 mm deep and 9.0 mm wide. Apex: Acute. Base: Cuneate. Margin: Entire. Texture: Pubescent (both surfaces). Color: Primarily RHS 145A on both surfaces with the outside tip and sometimes the margins being RHS N186C.
*Pistil.*—1; 32.0 mm long.
*Ovary.*—7.0 mm long and 3.0 mm wide; RHS 144C.
*Style.*—25.0 mm long and less than 1.0 mm wide; RHS NN155C.
*Stigma.*—RHS N200A.
*Stamen.*—5, one sterile without an anther; held within the corolla.
*Filament.*—2.5 to 4.0 cm long; RHS N155C.
*Anther.*—3.0 mm wide and 1.5 mm deep; RHS N186D.
*Pollen.*—Moderate quantity; RHS NN155C.

Fruit:

*Type.*—Capsule.
*Fertility.*—Good.
*Size.*—1.4 cm deep and 4.0 mm wide.
*Color.*—RHS N186C.

Seeds:

*Shape.*—Irregular.
*Size.*—2.0 mm long.
*Color.*—RHS 200A.

Pests/diseases: High resistance to root rot. No leaf spot, rust, or powdery mildew observed. No other unusual resistance or susceptibility noted to date.

I claim:

1. A new and distinct variety of *Penstemon* plant named 'Flock of Flamingos', substantially as illustrated and described herein.

* * * * *